United States Patent
Horiike (10) Patent No.: US 9,084,532 B2
(45) Date of Patent: Jul. 21, 2015

(54) MOTOR DRIVE APPARATUS AND IMAGING APPARATUS FOR DIAGNOSIS

(75) Inventor: Toyokazu Horiike, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 596 days.

(21) Appl. No.: 13/533,462

(22) Filed: Jun. 26, 2012

(65) Prior Publication Data

US 2013/0002843 A1    Jan. 3, 2013

(30) Foreign Application Priority Data

Jun. 30, 2011    (JP) .................................. 2011-146297

(51) Int. Cl.
| | | |
|---|---|---|
| *A61B 8/00* | (2006.01) | |
| *A61B 5/00* | (2006.01) | |
| *A61B 8/12* | (2006.01) | |
| *A61B 8/08* | (2006.01) | |

(52) U.S. Cl.
CPC ............. *A61B 5/0066* (2013.01); *A61B 5/0084* (2013.01); *A61B 8/12* (2013.01); *A61B 8/4209* (2013.01); *A61B 8/4455* (2013.01); *A61B 8/0891* (2013.01); *A61B 8/4461* (2013.01); *A61B 2560/0425* (2013.01); *A61B 2560/0431* (2013.01)

(58) Field of Classification Search
CPC ...... A61B 5/0066; A61B 8/4455; A61B 8/12; A61B 8/4209; A61B 5/0084; A61B 8/4461; A61B 8/0891; A61B 2560/0431; A61B 2560/0425

See application file for complete search history.

(56) References Cited

U.S. PATENT DOCUMENTS

| 5,810,733 | A | 9/1998 | Van Creveld et al. |
| 5,827,313 | A * | 10/1998 | Ream ............................ 606/171 |
| 5,957,941 | A | 9/1999 | Ream |
| 6,398,755 | B1 | 6/2002 | Belef et al. |
| 7,738,941 | B2 | 6/2010 | Hirota |
| 2008/0282846 | A1 | 11/2008 | Sharifi-Mehr et al. |

(Continued)

FOREIGN PATENT DOCUMENTS

| JP | 63-047266 U | 3/1988 |
| JP | 03-128048 A | 5/1991 |
| JP | 2011-072596 A | 4/2011 |

(Continued)

OTHER PUBLICATIONS

The extended European Search Report Issued on Oct. 9, 2012, by the European Patent Office in corresponding European Patent Application No. 12174219.1-1265. (7 pages).

(Continued)

*Primary Examiner* — Sath V Perungavoor
*Assistant Examiner* — Amadihe Kennon
(74) *Attorney, Agent, or Firm* — Buchanan Ingersoll & Rooney PC (57) ABSTRACT

A motor drive apparatus mounted with an imaging probe having a transmitting and receiving unit which carries out signal transmission and reception continuously, comprises: a scanner unit; a pull-back unit; and an operation unit, wherein on the side surface of the scanner unit, there are formed, at positions where facing each other, a convex portion formed for a predetermined length along the straight-ahead direction of the scanner unit, and a concave portion having an upper end surface which forms an identical surface as a lower end surface of the convex portion.

15 Claims, 7 Drawing Sheets

(56) References Cited

U.S. PATENT DOCUMENTS

2009/0264768 A1* 10/2009 Courtney et al. ............. 600/463
2012/0215091 A1 8/2012 Suzuki et al.

FOREIGN PATENT DOCUMENTS

| JP | 2011-072597 A | 4/2011 |
| WO | 9812967 A1 | 4/1998 |
| WO | 9812968 A1 | 4/1998 |

OTHER PUBLICATIONS

Extended European Search Report dated Dec. 5, 2012, issued by the European Patent Office in the corresponding European Application No. 121742191. (14 pages).

* cited by examiner

MOTOR DRIVE APPARATUS AND IMAGING APPARATUS FOR DIAGNOSIS

CROSS REFERENCES TO RELATED APPLICATIONS

The present invention contains subject matter related to Japanese Patent Application No. 2011-146297 filed in the Japanese Patent Office on Jun. 30, 2011, the entire contents of which is incorporated herein by reference.

TECHNICAL FIELD

The present invention generally relates to a motor drive apparatus and an imaging apparatus for diagnosis.

BACKGROUND DISCUSSION

In the past, to diagnose arterioscleosis, to perform diagnosis before a surgical operation or confirm a result after a surgical operation at the time of medical treatment inside a blood vessel by a highly-functional catheter such as a balloon catheter, a stent or the like, there has been utilized an imaging apparatus for diagnosis such as an intravascular ultrasound (IVUS) diagnostic apparatus, an optical coherent tomography (OCT) apparatus, an optical frequency domain imaging (OFDI) apparatus utilizing wavelength sweep, which is an improved type thereof, and the like (hereinafter, in this specification, the optical coherent tomography (OCT) apparatus and the optical frequency domain imaging (OFDI) apparatus utilizing wavelength sweep are referred to generically as "optical imaging apparatus for diagnosis").

In the optical imaging apparatus for diagnosis, an optical probe unit, into which an imaging core mounted with an optical lens and an optical mirror (transmitting and receiving unit) at the distal end of an optical fiber is positioned, is inserted inside a blood vessel, a measurement light is emitted into the inside of the blood vessel from the transmitting and receiving unit at the distal end while rotating the imaging core and concurrently, a radial scan inside the blood vessel is carried out by light-receiving a reflected light from a biological tissue. Then, based on the interference light generated by making the light-received reflected light and the reference light interfere, a cross-sectional image of the blood vessel is visualized.

Here, for the radial scan of the imaging core, there is utilized a motor drive apparatus referred to generally as a scanner & pull-back unit. The scanner & pull-back unit is constituted by a scanner unit and a pull-back unit, and the optical probe unit is freely detachably mounted on the scanner unit.

Then, for the scanner & pull-back unit mounted with the optical probe, various kinds of settings are carried out in an operating room or the like and thereafter, the unit is used under the condition of being covered by a unit cover (sterilization cover) and being moved to the vicinity of the patient.

In other words, in the inside of the operating room or the like, it is assumed for the scanner & pull-back unit to make the user (doctor, technologist, nurse or the like) move to a predetermined position if required, back away from the predetermined position and so on. Consequently, it is desirable for the scanner & pull-back unit to have a convenient shape to be carried. In particular, since the carrying of the scanner & pull-back unit is performed in a state of being covered by a unit cover, it is desirable for the unit to have a shape easily carried even in such a state.

In addition, from the fact that it is necessary to deal with a plurality of works during a short period inside the operating room, it is desirable, on an occasion of carrying the scanner & pull-back unit, that there are assumed not only a case in which the user carries out the unit by both hands but also a case in which the user carries out the unit by a single hand.

SUMMARY

A motor drive apparatus which is mounted with an imaging probe having a transmitting and receiving unit which carries out signal transmission and reception continuously comprises: a scanner unit configured to axially rotate the transmitting and receiving unit; A pull-back unit configured to operate the scanner unit to axially move the transmitting and receiving unit in a body lumen; the pull-back unit comprising two shelf portions spaced apart from each other in the lengthwise direction, with each of the shelf portions possessing a bottom surface spaced from the bottom surface of the pull-back unit so that a space underlies each of the shelf portions; and a side wall portion surrounding each of the shelf portions and upstanding from each of the shelf portions. The bottom surface of the pull-back unit includes two grooves spaced apart from each other in the lengthwise direction and each extending in the lengthwise direction, and the shelf portions and the grooves are configured to permit a user to grasp one of the shelf portions together with one of the grooves using fingers of one hand of the user and to grasp the other shelf portion together with the other groove using fingers of the user's other hand. A projecting part extends laterally outwardly from both side surfaces of the scanner unit, with each projecting part extending in the lengthwise direction of the scanner unit over only a portion of the lengthwise extent of the scanner unit; and a recess underlies each of the projecting parts so that each of the projecting parts forms a cantilevered ledge.

In accordance with another aspect, a motor drive apparatus mounted with an imaging probe having a transmitting and receiving unit which carries out signal transmission and reception continuously, comprises: a scanner unit configured to axially rotate the transmitting and receiving unit; a pull-back unit configured to operate the scanner unit in straight-ahead in order to axially move the transmitting and receiving unit in a body lumen; an operation unit comprising an instruction unit permitting instruction input to control the scanner unit and the pull-back unit, and an indicator indicating a state of the motor drive apparatus, with the instruction unit and the indicator being aligned on a side surface of the pull-back unit; an outwardly projecting convex portion on each of the opposite side surfaces of the scanner unit, with each convex portion extending in the lengthwise direction of the scanner unit over a predetermined length; a concave portion on each of the opposite side surfaces of the scanner unit opposite side surfaces of the scanner unit, with each concave portion extending in the lengthwise direction of the scanner unit over a predetermined length; and each concave portion having an upper end surface which also constitutes a lower end surface of one of the convex portions.

According to an additional aspect, a motor drive apparatus mounted with an imaging probe having a transmitting and receiving unit which carries out continuous signal transmission and reception continuously comprises: a scanner unit configured to axially rotate the transmitting and receiving unit, a pull-back unit configured to operate the scanner unit in straight-ahead in order to axially move the transmitting and receiving unit in a body lumen; an operation unit comprising an instruction unit permitting instruction input to control the scanner unit and the pull-back unit, and an indicator indicating a state of the motor drive apparatus, the instruction unit and the indicator being aligned on a side surface of the pull-back unit, with the operation unit being positioned only on one side surface of the pull-back unit; a shelf portion at the forward end of the pull-back unit and a shelf portion at the rear end of the pull-back unit, with each of the shelf portions possessing an upper surface and also possessing a bottom surface spaced from the bottom surface of the pull-back unit; a side wall portion surrounding each of the shelf portions, with each side wall portion possessing an upper end portion higher than the upper surface of the shelf portion; and the bottom surface of the pull-back unit at the forward end of the pull-back unit including a groove, and the bottom surface of the pull-back unit at the rear end of the pull-back unit including a groove, each groove extending for a predetermined length along the straight-ahead direction of the scanner unit, the grooves being located at an approximately center position relative to a direction perpendicular to the straight-ahead direction.

According to the above aspects, in a motor drive apparatus of an imaging apparatus for diagnosis, it becomes possible to provide a shape convenient for being carried under the use condition thereof.

DETAILED DESCRIPTION

The description which follows describes, with reference to the accompanying drawings, details and aspects of embodiments of an optical imaging apparatus, including a canner & pull-back unit, disclosed as examples.

First, there will be explained a brief summary of the motor drive apparatus, i.e., scanner & pull-back unit, according to a first embodiment. The motor drive apparatus has a shape configured in the manner described so it exhibits a convenient shape to be carried under an actual use condition.

In case of carrying it by a single hand, it is assumed that the user may grasp and hold the side surface center position of the scanner unit from the upper side of the unit, and there is employed a configuration in which a concave portion (and a convex portion) for hooking a fingertip (of a thumb and/or another finger) is provided such that the scanner unit does not slip off when being grasped and held from the upper side thereof. Also, in order to make it easier to recognize the grasping and holding position even in a state of being covered by a unit cover, a configuration is employed in which a convex portion is provided. Further, in order to avoid a situation in which the instruction unit arranged on the side surface of the pull-back unit is pressed accidentally when grasping and holding the scanner unit from the upper side thereof, there is employed a configuration in which the instruction unit is arranged at a deviated position with respect to the position to be grasped and held. It is possible, within the instruction unit, to arrange an instruction button which does not exert influence on the operation of the pull-back unit even if pressed.

In case of carrying it by both hands, it is assumed that the user may support the lower surface of both the end positions in the forward and backward direction of the pull-back unit from the lower side and so there is employed a shape by which it is relatively easy for a fingertip to be slipped into the lower surface of the pull-back unit even in a state in which the scanner unit is installed. Also, there is employed a configuration in which a concave portion hooked by fingertips (thumb and other finger) is provided such that a situation does not arise in which it slips off from both hands.

By employing such a configuration, for the motor drive apparatus relating to this embodiment disclosed by way of example, there is created a situation in which the carrying thereof can be performed relatively easily by a single hand or by both hands in a state of being covered by the unit cover. Hereinafter, there will be explained details of this embodiment.

1. Overall Configuration of Optical Imaging Apparatus for Diagnosis

Figure 1:
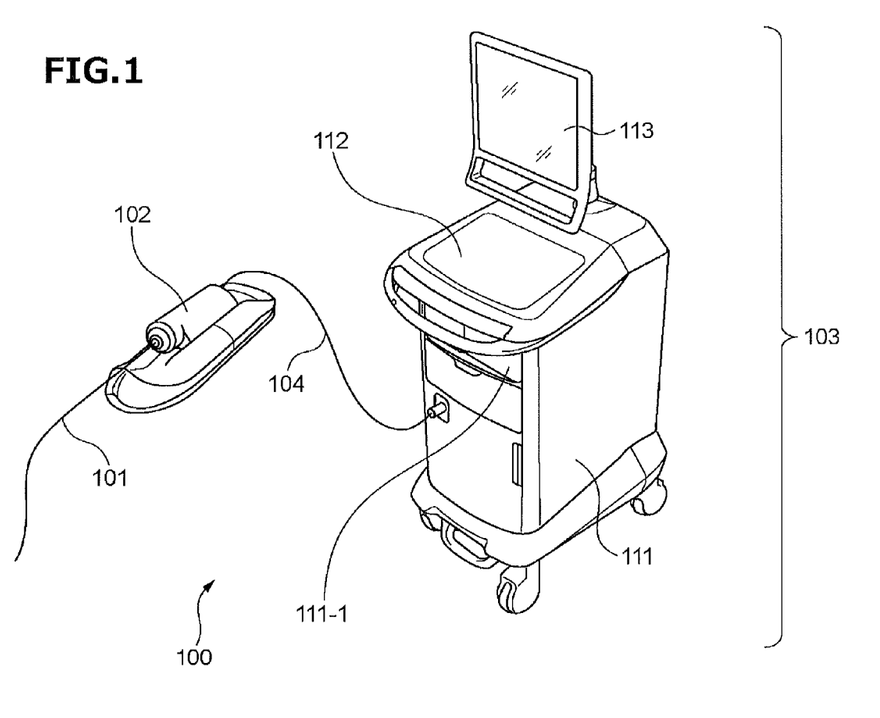
FIG. 1 is a perspective view of an optical imaging apparatus for diagnosis according to one embodiment disclosed by way of example.

First, there will be explained an optical imaging apparatus for diagnosis provided with a motor drive apparatus. FIG. 1 illustrates the configuration of the overall optical imaging apparatus for diagnosis (optical coherent tomography (OCT) apparatus or optical frequency domain imaging (OFDI) apparatus utilizing wavelength sweep) 100 provided with a motor drive apparatus.

As shown in FIG. 1, the optical imaging apparatus for diagnosis 100 includes an optical probe unit (imaging probe) 101, a motor drive apparatus 102 and an operation control apparatus 103. The motor drive apparatus 102 and the operation control apparatus 103 are connected by a signal line 104.

The optical probe unit 101 is installed with an imaging core provided, at the distal end thereof, with a transmitting and receiving unit which is directly inserted into the inside of a body lumen such as a blood vessel or the like, transmits the transmitted measurement light continuously toward the biological tissue and concurrently, receives the reflected light continuously from the biological tissue, whereupon the state of the biological tissue is measured by using the imaging core. The optical probe unit 101 thus functions as an image obtaining probe unit for obtaining an image of the biological tissue.

The motor drive apparatus (scanner & pull-back unit) 102 is configured such that the optical probe unit 101 is freely detachably mounted on the motor drive apparatus 102. A radial operation (operation in axis direction and operation in rotation direction inside the body lumen) of the imaging core inserted into the optical probe unit 101 is performed by driving the built-in motor. The reflected light is received by the transmitting and receiving unit and concurrently the obtained reflected light is transmitted to the operation control apparatus 103 through the signal wire 104. Details of the shape or configuration of the motor drive apparatus 102 will be described below.

The operation control apparatus 103 is configured to allow the input of various kinds of setting values when carrying out the measurement, to process data obtained by the measurement and to display them as the cross-sectional image of the biological tissue.

The operation control apparatus 103 includes a main body control unit, whereby interference light data are generated by making the reflected light obtained by the measurement and the reference light obtained by separating the measurement light interfere, and concurrently a plurality of cross-sectional images are generated in the axial direction of the body lumen by processing the line data generated based on the interference light data. The operation control apparatus 103 also includes a printer 111-1 so that the result processed in the main body control unit 111 is printed. The operation control apparatus 103 is also provided with a hard disk drive and a DVD recorder for storing data.

An operation panel 112 allows a user to input various kinds of setting values and instructions. An LCD monitor 113 constitutes an example of a display apparatus that displays a plurality of cross-sectional images generated in the main body control unit 111.

2. Overall Configuration of Motor Drive Apparatus

Figure 2:
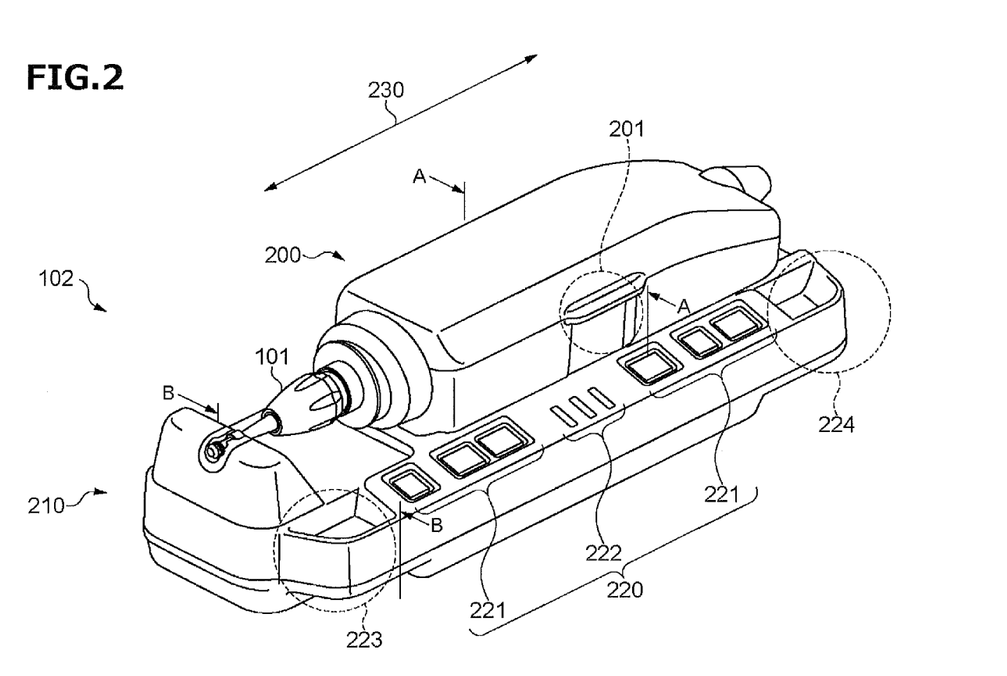
FIG. 2 is a perspective view of a scanner & pull-back unit forming a part of the apparatus shown in FIG. 1.

Referring to FIG. 2, set forth next is a description of the overall configuration of the motor drive apparatus 102 according to one embodiment disclosed by way of example. As shown in FIG. 2, the motor drive apparatus 102 is detachably mounted on the optical probe unit 101 and is provided with a scanner unit 200 for axially rotating the imaging core inserted into the optical probe unit 101, and a pull-back unit 210 for making the imaging core inserted into the optical probe unit 101 operate in the axial direction inside a body lumen by operating the scanner unit 200 in a straight-ahead manner in the direction of the arrow 230.

A motor forms a part of the scanner unit 200. Such motor carries out rotation operation to rotate the imaging core at a maximum rotation speed of 9600 rpm. On the other hand, the pull-back unit 210 incorporates a motor for straight-ahead operation for operating the imaging core in the axial direction inside the body lumen by operating the scanner unit 200 in a straight-ahead manner. Note that an operation unit 220 is provided on the side surface (right upper side in the drawing) of the pull-back unit 210.

The operation unit 220 includes an instruction unit 221 for instructing the rotation operation and the straight-ahead operation of the motor drive apparatus 102, and for instructing various kinds of settings, and thus, it is possible for the user to instruct the motor drive apparatus 102 to perform a desirable operation. The operation unit 220 also includes various kinds of lamps or lights 222, forming an indicator indicating the inside state of the motor drive apparatus 102 and thus, in a case in which an anomaly occurs in the motor drive apparatus 102, it is possible for the user to recognize this anomaly.

The motor drive apparatus 102 having such operational characteristics includes a mechanism (portable mechanism for single hand 201), which facilitates carrying the motor drive apparatus 102 by a single hand, on the center position side surface in the arrow 230 direction (straight-ahead direction) of the scanner unit 200. That is, the portable mechanism for single hand 201 is positioned at a center location relative to the front-back direction represented by the arrow 230. FIG. 2 illustrates the portable mechanism for single hand 201 arranged on the right side, but a similar mechanism is arranged on the opposite side so that a pair of portable mechanisms for single hand 201 exists on opposite sides of the motor drive apparatus 102.

The motor drive apparatus 102 also includes mechanisms (portable mechanisms for both hands 223, 224) which facilitate carrying the motor drive apparatus 102 by both hands on the side surface of the pull-back unit 210. Although not shown in FIG. 2, there are further provided mechanisms which facilitate carrying the motor drive apparatus 102 by both hands on the bottom surface of the pull-back unit 210.

3. Details of Portable Mechanism for Single Hand in Motor Drive Apparatus

Figure 3A:
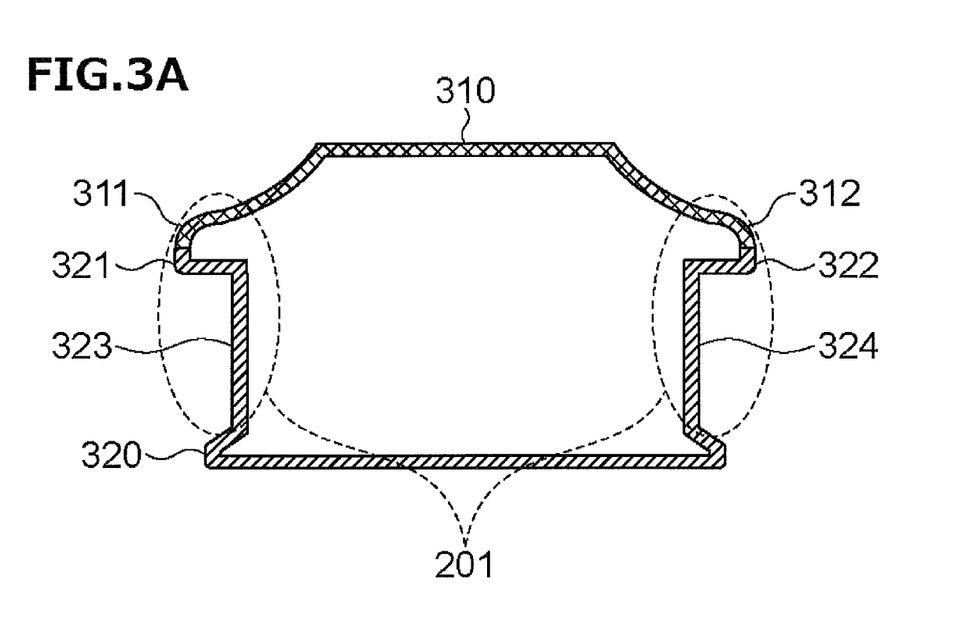
FIG. 3A is a cross-sectional view of a scanner unit taken along the section line 3A-3A in FIG. 2.

Set forth next, with reference to FIG. 3A is an explanation of details of the portable mechanism for single hand 201. FIG. 3A illustrates in cross-section the housing of the scanner unit 200. FIG. 3 does not illustrate the pull-back unit 210.

As shown in FIG. 3A, the housing of the scanner unit 200 includes an upper housing portion 310 and a lower housing portion 320. A convex portion (outwardly projecting part) 311 and a convex portion (outwardly projecting part) 312 are provided on opposite side surfaces of the upper housing portion 310. A convex portion (outwardly projecting part) 321 and a convex portion (outwardly projecting part) 322 are also provided on opposite side surfaces of the lower housing portion 320. The convex portion 311 and the convex portion 321 are formed so as to be continuous with one another. Similarly, the convex portion 312 and the convex portion 322 are formed so as to be continuous with one another.

Providing the convex portions on the side surface of the housing of the scanner unit 200 makes it possible to recognize the position at which the motor drive apparatus 102 should be grasped and held when the user sees the unit from above, even in a state in which the scanner unit 200 is covered by the unit cover.

A reason for employing a configuration in which the convex portion 311 of the upper housing portion 310 and the convex portion 321 of the lower housing portion 320 are combined (and the convex portion 312 of the upper housing 310 and the convex portion 322 of the lower housing 320 are combined) to form the convex portion (projection) on the side surface of the scanner unit 200 is to suppress bending of the side surface of the housing of the scanner unit 200 when being grasped and held by the user so that the carrying becomes easier.

The side surface of the lower housing 320 is further provided with a concave portion (recess) 323 and a concave portion (recess) 324. A common surface forms the upper end surface of the concave portion (recess) 323 and the lower end surface of the convex portion (outwardly projecting part) 321. That is, the upper end surface of the concave portion (recess) 323 and the lower end surface of the convex portion (outwardly projecting part) 321 are the same surface. Similarly, a common surface forms the upper end surface of the concave portion (recess) 324 and the lower end surface of the convex portion (outwardly projecting part) 322 so that the upper end surface of the concave portion 324 and the lower end surface of the convex portion 322 represent the same surface. The convex portion 321 together with the underlying recess 323 form a projection or ledge which projects in a cantilever manner on one of the side surfaces of the scanner unit. Similarly, the convex portion 322 together with the underlying recess 324 form a projection or ledge which projects in a cantilever manner on the opposite side surface of the scanner unit.

Employing a configuration in which the concave portion exists in the side surface of the housing of the scanner unit 200 provides an arrangement in which the user's fingertips (thumb and other finger) are hooked on the end surface of the concave portion (and end surface of the convex portion) when the scanner unit 200 is grasped and held from the upper side, whereby the carrying thereof becomes easy.

Figure 3B:
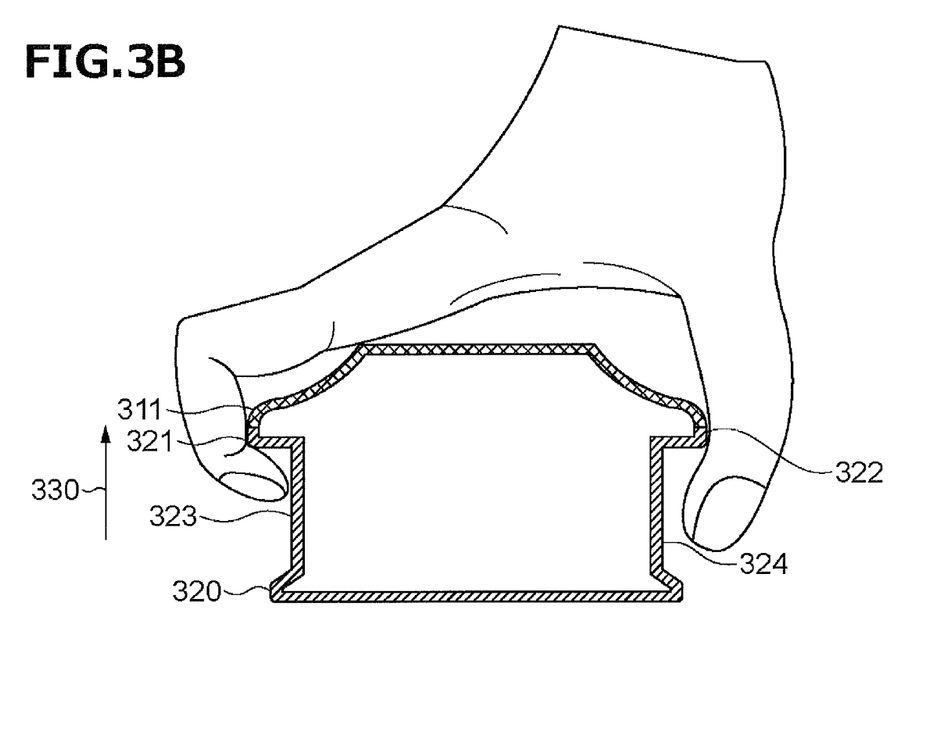
FIG. 3B illustrates a way of carrying the scanner & pull-back unit by grasping and holding the scanner unit.

FIG. 3B illustrates the scanner unit 200 while grasped and held from the upper side. As shown in FIG. 3B, the tip of the user's index finger (and any other finger(s) except the thumb) is inserted into the concave portion (recess) 323 and so the periphery of the first joint of the user's finger contacts the upper end surface of the concave portion 323 and the lower end surface of the convex portion 321 which is formed integrally with the upper end surface of the concave portion 323. It thus becomes possible to avoid a situation in which the motor drive apparatus 102 slips from the user's fingertips while being lifted up in the direction of the arrow 330.

Similarly, the tip of the user's thumb is positioned in the concave portion 324 so that the first joint of the user's finger contacts the upper end surface of the concave portion 324 and the lower surface of the convex portion 322 which is formed integrally with the upper end surface of the concave portion 324. This makes it possible to avoid a situation in which the motor drive apparatus 102 slips from the fingertips while being lifted up in the direction of the arrow 330.

The portable mechanism for single hand 201 is arranged at the center position in the arrow 230 direction of the scanner unit 200 such that the portable mechanism for single hand 201 is at approximately a balanced position in the arrow 230 direction of the motor drive apparatus 102 in a state in which the scanner unit 200 has moved to the advanced end position.

4. Details of Portable Mechanism for Both Hands in Motor Drive Apparatus

Figure 4A:
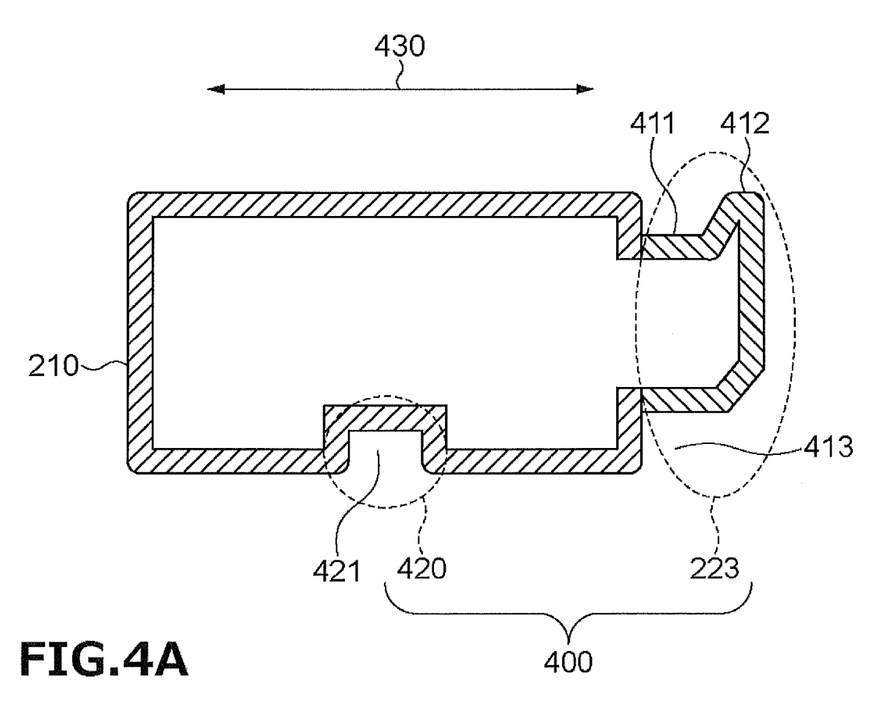
FIG. 4A is a cross-sectional view of the pull-back unit taken along the section line 4A-4A in FIG. 2.

Set forth next, with reference to FIG. 4A, is a detailed description of aspects of a portable mechanism for both hands. FIG. 4A is a cross-section of the housing of the pull-back unit 210 in FIG. 2. The scanner unit 200 is not shown in FIG. 4A. As shown in FIG. 2, the portable mechanism for both hands is provided at both end positions of the pull-back unit 210 in the direction of the arrow 230, but both sides have similar configurations. Thus, the description which follows will describe the configuration of the distal position, it being understood that the configuration at the opposite end is the same.

As shown in FIG. 4A, a portable mechanism for both hands 400 is constituted by a first portable mechanism for both hands 223 provided on the side surface of the pull-back unit 210 (side surface on the side on which the operation unit 220 is arranged) and a second portable mechanism for both hands 420 provided on the bottom surface of the pull-back unit 210.

The first portable mechanism for both hands 223 includes a shelf portion 411 which extends outwardly (laterally) from the side surface of the pull-back unit 210 and an upstanding side wall portion 412 which surrounds the periphery of the shelf portion 411. The shelf portion 411 has a predetermined height with respect to (is spaced from) the bottom surface of the pull-back unit 210. That is, the bottom surface of the shelf portion 411 is spaced from the bottom surface of the pull-back unit 210 so that a space 413 exists on the lower side of the shelf portion 411. Also, the upper end portion (upper surface) of the side wall portion 412 is higher than the upper surface of the shelf portion 411 and so a concave portion or recessed portion is formed by the upper surface of the shelf portion 411 and the encircling upper end portion of the side wall portion 412.

Providing the side wall portion 412 with respect to the shelf portion 411 which extends outwardly from the side surface of the pull-back unit 210, makes it possible for the user to hook a thumb when supporting the pull-back unit 210 from the lower side, whereby the carrying of the pull-back unit 210 becomes easier. Also, providing the space 413 on the lower side of the shelf portion 411 makes it possible to insert the user's fingertips relatively easily when the user's fingertips (fingertips of fingers except thumb) are inserted into the bottom surface of the pull-back unit 210 in order to support the pull-back unit 210 from the lower side.

Approximately at the center position in the direction of the arrow 430 (the direction approximately perpendicular to the direction of the arrow 230 direction in FIG. 2) of the bottom surface of the pull-back unit 210, there is further arranged a groove portion 421 along the arrow 230 direction. The groove portion 421 constitutes the second portable mechanism for both hands 420. Employing a configuration in which the groove portion 421 is arranged at the center position of the bottom surface of the pull-back unit 210 makes it possible for the user to hook the index finger and the like when the pull-back unit 210 is supported from the lower side, whereby the carrying thereof becomes easier. The length of the groove portion 421 in the arrow 230 direction can be configured such that it becomes possible for two to four of the user's fingers to be inserted into the groove portion 421.

Figure 4B:
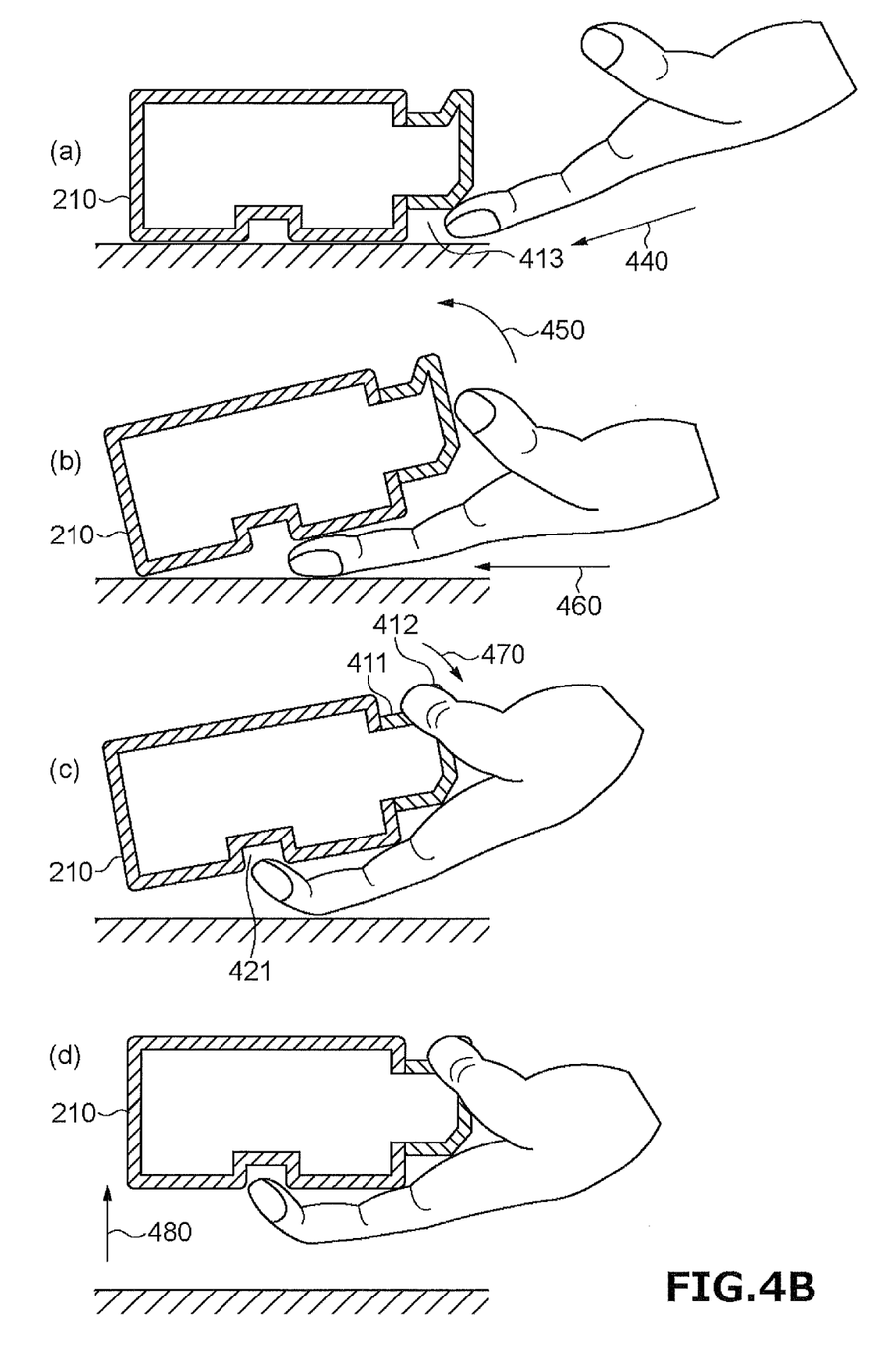
FIG. 4B illustrates a way of carrying the scanner & pull-back unit by supporting the pull-back unit.

FIG. 4B illustrates the pull-back unit 210 supported from the lower side. As shown in FIG. 4B, by inserting the tip of the user's index finger (any of other fingers except thumb) toward the direction of the arrow 440 with respect to the space 413 (see (a) of FIG. 4B), the motor drive apparatus 102 rotates in an arrow 450 direction as a whole (see (b) of FIG. 4B). Thus, it is possible to insert fingers (fingers except thumb) toward an arrow 460 direction relatively easily with respect to the bottom surface of the pull-back unit 210.

When the user's fingers are inserted toward the bottom surface of the pull-back unit 210 and the tips of the user's fingers reach the groove portion 421, it is possible for the user to hook the fingertips on the side surface of the groove portion 421 by bending the fingertips. On the other hand, by bending the thumb after inserting the thumb toward the upper surface of the shelf portion 411, the periphery of the first joint of the user's thumb contacts the side wall portion 412. Thus, there is created a situation in which the pull-back unit 210 rotates slightly toward the arrow 470 direction and the pull-back unit 210 is held stably by fingers other than thumb, which are hooked on the side surface of the groove portion 421, and the thumb hooked on the side wall portion 412 (see (c) of FIG. 4B).

In this state, by lifting up the pull-back unit 210 in the arrow 480 direction, it becomes possible to support the motor drive apparatus 102 from the lower side by both hands without the motor drive apparatus 102 slipping off from the fingertips (see (d) of FIG. 4B).

There are various reasons why the first portable mechanism for both hands 223 is provided on the side surface of the pull-back unit 210 and on the side surface on the side on which the operation unit 220 is arranged. After operating the operation unit 220, it is possible for the user to carry the unit directly by inserting his fingertips along the bottom surface of the pull-back unit 210 without changing the direction of the motor drive apparatus 102. Compared with the pull-back unit 210 in which a motor and the like exist, the operation unit 220 has only buttons and wirings, whereby the weight thereof is relatively light, so that it is fairly easy to rotate the unit in the arrow 450 direction.

5. Configuration of Operation Unit in Motor Drive Apparatus

Figure 5:
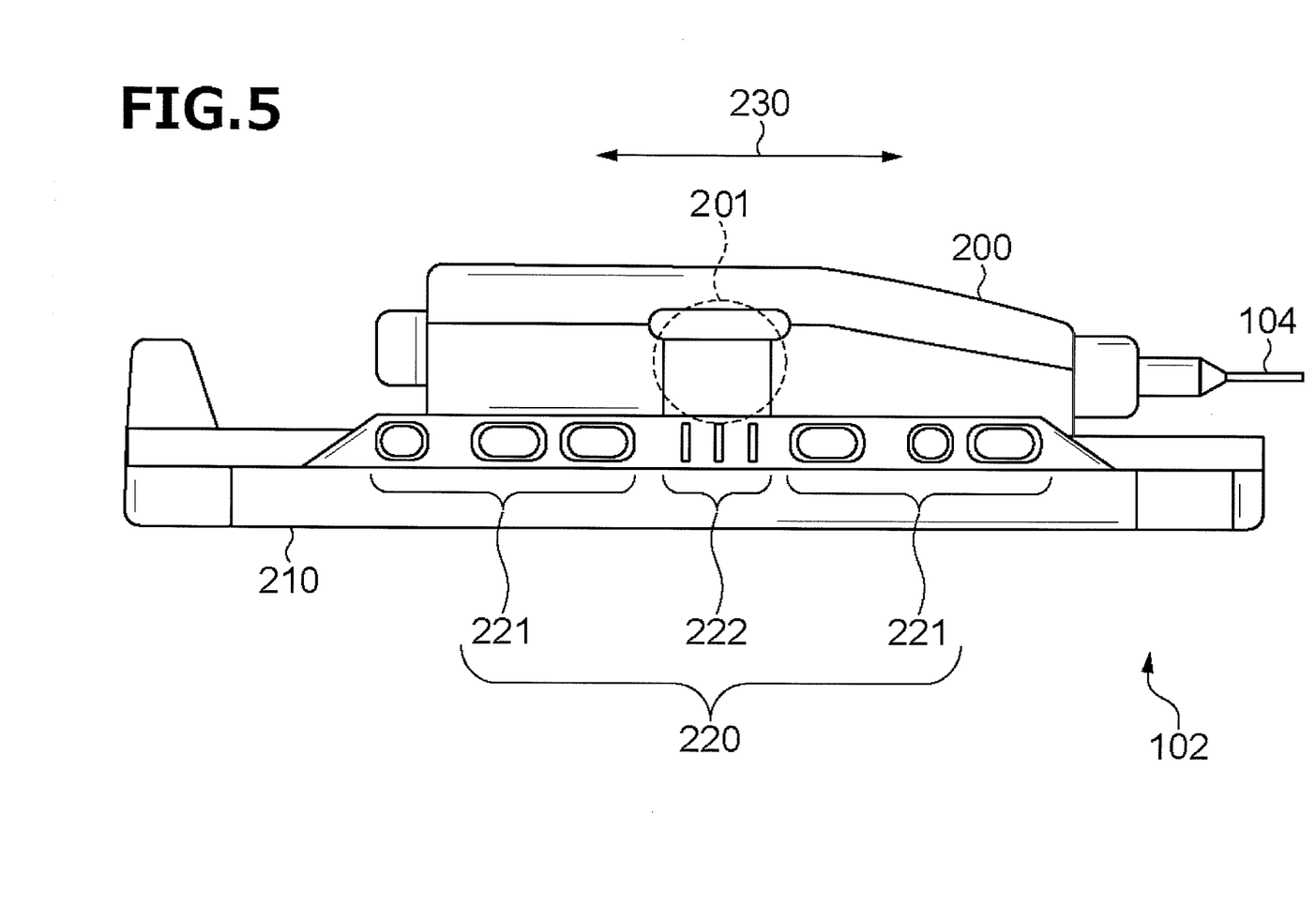
FIG. 5 is a side view of the scanner & pull-back unit.

Set forth next, with reference to FIG. 5, is a description of the configuration of the operation unit 220 in the motor drive apparatus. FIG. 5 shows the motor drive apparatus 102 seen from the side surface, with the optical probe unit 101 not yet mounted. In FIG. 5, the scanner unit 200 lies at the advanced end position in the arrow 230 direction. In the abovementioned position, the portable mechanism for single hand 201 is positioned approximately at a center position in the arrow 230 direction of the pull-back unit 210.

On the other hand, in the operation unit 220, only various kinds of lamps 222 are arranged at the abovementioned center position and the instruction unit 221 is aligned in the position other than the center position. In this manner, in the motor drive apparatus 102 relating to this embodiment disclosed by way of example, there is employed such a configuration, in a state in which the scanner unit 200 lies at the advanced end position and in which it is possible for the motor drive apparatus 102 to be carried, that the instruction unit 221 is not located at the position corresponding to the portable mechanism for single hand 201.

Thus, when the scanner unit 200 is grasped and held from the upper side, it becomes possible to avoid a situation in which the instruction unit is pressed erroneously. It is possible to provide an instruction button which does not have any operational problem even if pushed down erroneously, that is, to provide a button having nothing to do with the operation of the pull-back unit, corresponding to the portable mechanism for single hand 201. For example, it is possible to install an instruction button (scan button) by which the imaging core is rotated at a low speed as idling before the pull-back.

As clear from the explanation above, the motor drive apparatus 102 according to this embodiment employs a configuration in which the concave portions or recesses (and convex portions or projections) for hooking fingertips (thumb and other fingers) are provided so as not to be slipped off when supported from the upper side on the assumption that the user grasps and holds the center position of the side surface of the scanner unit from the upper side while being carried by a single hand. Also, there is employed a configuration in which the convex portions or projections are provided so as to recognize the grasping and holding position relatively easily even in a state in which the unit is covered by the unit cover. Furthermore, a configuration is employed in which the instruction unit is displaced or shifted such that a situation will not occur in which the instruction unit is pressed erroneously when the motor drive apparatus 102 is grasped and held from the upper side. In case of being carried by both hands, there is employed a shape by which it is relatively easy for the fingertips to slip along the lower surface fairly easily even in a state in which the motor drive apparatus is placed so that the lower surfaces of both the end positions in the forward and backward directions of the pull-back unit will be supported from the lower side. Also, the concave portions (or groove portions) for hooking fingertips (thumb and other finger) are provided such that the unit does not slip off from both the hands when supported from the lower side.

According to this result, the carrying becomes relatively easy under the actual use environment.

In the above-mentioned first embodiment, a configuration is employed in which both the portable mechanism for single hand and the portable mechanism for both hands are provided, but the present invention is not limited in this regard as it is possible to employ a construction which includes only one of the two mechanisms.

The description above does not describe specific materials for the portable mechanism for single hand 201 or the portable mechanism for both hands 400. But possible, for example, to employ a configuration in which anti-slip rubber is disposed on the upper end surfaces of the concave portions 323, 324 and the lower end surfaces of the convex portions 321, 322 of the portable mechanism for single hand 201. Similarly, it is possible to employ a configuration in which anti-slip rubber is disposed on the side wall portion 412 and on the groove portion 421 in the portable mechanism for both hands 400.

The embodiment described above by way of example refers to an optical imaging apparatus for diagnosis as an example. It is also possible to apply the disclosure here to an imaging apparatus for diagnosis using an ultra-sound probe (image obtaining probe unit) which uses ultra-sound instead of light.

The detailed description above describes features and aspects of an embodiment of a motor drive apparatus and an imaging apparatus for diagnosis disclosed by way of example. But the invention is not limited to the precise embodiments and variations described. Changes, modifications and equivalents can be effected by one skilled in the art without departing from the spirit and scope of the invention as defined in the appended claims. It is expressly intended that all such changes, modifications and equivalents which fall within the scope of the claims are embraced by the claims.

What is claimed is:

1. A motor drive apparatus mounted with an imaging probe having a transmitting and receiving unit which carries out continuous signal transmission and reception continuously comprising:
    a scanner unit configured to axially rotate the transmitting and receiving unit, the scanner unit extending over a lengthwise extent and possessing opposite side surfaces which each extend in a lengthwise direction of the scanner unit;
    a pull-back unit configured to operate the scanner unit to axially move the transmitting and receiving unit in a body lumen, the pull-back unit possessing opposite ends in the lengthwise direction of the scanner unit, the pull-back unit also possessing a bottom surface;
    the pull-back unit comprising two shelf portions spaced apart from each other in the lengthwise direction, each of the shelf portions possessing a bottom surface spaced from the bottom surface of the pull-back unit so that a space underlies each of the shelf portions;
    a side wall portion surrounding each of the shelf portions and upstanding from each of the shelf portions;
    the shelf portions being configured to permit a user to grasp one of the shelf portions using at least one finger of one of the user's hand and to grasp the other shelf portion using at least one finger of the user's other hand;
    a par of projecting parts each extending laterally outwardly from both side surfaces of the scanner unit, each projecting part extending in the lengthwise direction of the scanner unit over only a portion of the lengthwise extent of the scanner unit so that each of the projecting parts forms a cantilevered ledge; and
    the two projecting parts being configured to permit a user to grasp the two projecting parts using fingers of one of the user's hands.

2. The motor drive apparatus according to claim 1, wherein the pull-back unit includes an instruction unit permitting instruction input to control the scanner unit and the pull-back unit, the instruction unit being positioned between the two shelf portions in the lengthwise direction.

3. The motor drive apparatus according to claim 2, wherein the pull-back unit includes at least one lamp indicating a state of the motor drive apparatus, the instruction unit and the at least one lamp being aligned on one of the side surfaces of the pull-back unit.

4. The motor drive apparatus according to claim 1, wherein the pull-back unit includes at least one lamp indicating a state of the motor drive apparatus and a plurality of buttons permitting instruction input to control the scanner unit and the pull-back unit, the buttons and the at least one lamp being positioned on one of the side surfaces of the pull-back unit and between the two shelf portions in the lengthwise direction.

5. The motor drive apparatus according to claim 1, wherein the grooves are located at an approximately center position relative to a direction perpendicular to the lengthwise direction.

6. The motor drive apparatus according to claim 1, wherein each of the recesses possesses an upper surface which also constitutes a lower end surface of one of the projecting parts.

7. The motor drive apparatus according to claim 1, wherein the bottom surface of the pull-back unit includes two grooves spaced apart from each other in the lengthwise direction, the two grooves being configured to permit the user to grip one of the grooves together with the one shelf portion using fingers of the user's one hand and to grip the other groove together with the other shelf portion using fingers of the user's other hand.

8. A motor drive apparatus mounted with an imaging probe having a transmitting and receiving unit which carries out continuous signal transmission and reception comprising:
- a scanner unit configured to axially rotate the transmitting and receiving unit, the scanner unit possessing opposite side surfaces each extending in a lengthwise direction of the scanner unit;
- a pull-back unit configured to operate the scanner unit in straight-ahead in order to axially move the transmitting and receiving unit in a body lumen;
- an operation unit comprising an instruction unit permitting instruction input to control the scanner unit and the pull-back unit, and an indicator indicating a state of the motor drive apparatus, the instruction unit and the indicator being aligned on a side surface of the pull-back unit;
- an outwardly projecting convex portion on each of the opposite side surfaces of the scanner unit, each convex portion extending in the lengthwise direction of the scanner unit over a predetermined length;
- a concave portion on each of the opposite side surfaces of the scanner unit opposite side surfaces of the scanner unit, each concave portion extending in the lengthwise direction of the scanner unit over a predetermined length; and
- each concave portion having an upper end surface which also constitutes a lower end surface of one of the convex portions.

9. The motor drive apparatus according to claim 8, wherein the instruction unit comprises buttons, all of the buttons related to operation of the pull-back unit are located at positions not aligned in the lengthwise direction of the scanner unit with the convex portions in a state in which the scanner unit is located at an advanced end position of the scanner unit.

10. The motor drive apparatus according to claim 8, wherein each of the convex portions is located in a middle of the scanner unit in the lengthwise direction of the scanner unit.

11. An imaging apparatus for diagnosis comprising the motor drive apparatus according to claim 8, wherein a plurality of cross-sectional images in the axis direction of the body lumen are generated based on a signal transmitted from the motor drive apparatus.

12. A motor drive apparatus mounted with an imaging probe having a transmitting and receiving unit which carries out continuous signal transmission and reception continuously comprising:
- a scanner unit configured to axially rotate the transmitting and receiving unit, the scanner unit possessing opposite side surfaces each extending in a straight-ahead direction of the scanner unit;
- a pull-back unit configured to operate the scanner unit in straight-ahead in order to axially move the transmitting and receiving unit in a body lumen, the pull-back unit possessing a forward end and an oppositely located rear end in the straight-ahead direction of the scanner unit, the pull-back unit also possessing a bottom surface;
- an operation unit comprising an instruction unit permitting instruction input to control the scanner unit and the pull-back unit, and an indicator indicating a state of the motor drive apparatus, the instruction unit and the indicator being aligned on a side surface of the pull-back unit;
- the operation unit being positioned only on one side surface of the pull-back unit;
- a shelf portion at the forward end of the pull-back unit and a shelf portion at the rear end of the pull-back unit;
- each of the shelf portions possessing an upper surface and also possessing a bottom surface spaced from the bottom surface of the pull-back unit;
- a side wall portion surrounding each of the shelf portions, each side wall portion possessing an upper end portion higher than the upper surface of the shelf portion; and
- the bottom surface of the pull-back unit at the forward end of the pull-back unit including a groove, and the bottom surface of the pull-back unit at the rear end of the pull-back unit including a groove, each groove extending for a predetermined length along the straight-ahead direction of the scanner unit, the grooves being located at an approximately center position relative to a direction perpendicular to the straight-ahead direction.

13. The motor drive apparatus according to claim 12, wherein the instruction unit is positioned entirely between the shelf portions relative to the straight-ahead direction.

14. The motor drive apparatus according to claim 12, wherein the instruction unit comprises a plurality of user operable buttons, and the indicator comprises a plurality of lamps.

15. An imaging apparatus for diagnosis comprising the motor drive apparatus according to claim 12, wherein a plurality of cross-sectional images in the axis direction of the body lumen are generated based on a signal transmitted from the motor drive apparatus.

* * * * *